(12) United States Patent
Yang et al.

(10) Patent No.: US 11,913,002 B2
(45) Date of Patent: Feb. 27, 2024

(54) MODIFIED PLANT ENDOSPERM SPECIFIC PROMOTER AND USE THEREOF

(71) Applicant: WUHAN HEALTHGEN BIOTECHNOLOGY CORP., Wuhan (CN)

(72) Inventors: Daichang Yang, Wuhan (CN); Kunpeng Li, Wuhan (CN)

(73) Assignee: WUHAN HEALTHGEN BIOTECHNOLOGY CORP., Wuhan (CN)

( * ) Notice: Subject to any disclaimer, the term of this patent is extended or adjusted under 35 U.S.C. 154(b) by 0 days.

(21) Appl. No.: 18/032,130

(22) PCT Filed: Aug. 17, 2021

(86) PCT No.: PCT/CN2021/112887
§ 371 (c)(1),
(2) Date: May 10, 2023

(87) PCT Pub. No.: WO2022/078049
PCT Pub. Date: Apr. 21, 2022

(65) Prior Publication Data
US 2023/0383302 A1    Nov. 30, 2023

(30) Foreign Application Priority Data
Oct. 16, 2020    (CN) .......................... 202011109663.9

(51) Int. Cl.
| C12N 15/82 | (2006.01) |
| A01H 5/10 | (2018.01) |
| A01H 6/46 | (2018.01) |
| C07K 14/765 | (2006.01) |

(52) U.S. Cl.
CPC ........... *C12N 15/8205* (2013.01); *A01H 5/10* (2013.01); *A01H 6/46* (2018.05); *C07K 14/765* (2013.01); *C12N 15/8234* (2013.01); *C12N 2800/22* (2013.01)

(58) Field of Classification Search
None
See application file for complete search history.

(56) References Cited

U.S. PATENT DOCUMENTS

2007/0289033 A1* 12/2007 Yang et al. ........ C12N 15/8257
                                                                435/468
2018/0194801 A1* 7/2018 Yang et al. .......... B01J 20/3285

OTHER PUBLICATIONS

Saha et al. (2007) In Silico Biol 7(1):7-19.*
Potenza et al. (2004) In Vitro Cell Dev Biol Plant 40:1-22.*
Qu et al. (2008) J Exp Botany 59(9): 2417-24.*
Yamada et al. (2016) Sci Rep 6:36782.*

* cited by examiner

*Primary Examiner* — Russell T Boggs
(74) *Attorney, Agent, or Firm* — Greer, Burns & Crain, Ltd.; Gregory P. Einhorn

(57) ABSTRACT

Provided is a modified rice endosperm-specific promoter, which has a sequence as shown in any one of SEQ ID. NOs. 1 to 5. The EnhGt13α promoter as shown in SEQ ID NO. 2 drives GUS activity in vitro and mediates the expression of foreign proteins in rice endosperm cells, which is significantly higher than that of the unmodified Gt13α promoter. The promoter can be applied to the fields of improving seed quality, molecular pharming, etc.

20 Claims, 4 Drawing Sheets
Specification includes a Sequence Listing.

MODIFIED PLANT ENDOSPERM SPECIFIC PROMOTER AND USE THEREOF

FIELD OF THE INVENTION

The present invention belongs to the field of genetic engineering and biotechnology, and relates in particular to an artificially modified plant endosperm-specific promoter EnhGt13α and the use thereof.

BACKGROUND OF THE INVENTION

The expression and production of various recombinant proteins in plant cells through plant genetic engineering is also known as molecular pharming, and the recombinant protein products are known as plant-made pharmaceutical (PMP). At present, recombinant drugs successfully expressed in genetically engineered plants include hormones, antibodies, enzymes, cytokines, plasma protein factors and vaccines. Molecular pharming has shown many advantages in recombinant protein production, especially rice endosperm as an ideal recombinant protein expression system that has the following advantages: 1) As a model plant, rice has a clear genetic background and detailed genomic information; 2) Mature genetic transformation technology; 3) Rice is self-pollinated and the frequency of cross-pollination is very low, usually less than 1-5%, and the frequency of gene drift is only 0.036%, and the pollen loses its activity at 5 min after leaving the anther, and it has a good biosafety; 4) Rice seeds provide a ideal storage place for recombinant proteins after maturation and dehydration, in which the recombinant proteins are not easily degraded; 5) The seeds could be stored for long-term storage; 6) Rice endosperm contains a few types of storage proteins with low solubility, which benefit to the isolation and purification of target proteins; 7) Recent studies have shown that recombinant glycoproteins produced in rice endosperm exhibit low immunogenicity; 8) Rice is easier to grow and manage in the field, which facilitates the large-scale cultivation of genetically engineered rice.

The expression level of recombinant proteins directly affects product cost and market competitiveness, and is the key to influence whether the PMP product can enter the market. Therefore, the continuous improvement of recombinant protein expression is a constant theme in molecular pharming research. In the past two decades, in order to improve the expression level of recombinant proteins in plant cells, extensive research has been conducted and much progress has been made. The strategies to improve the expression of recombinant proteins mainly focus on the following aspects: 1) using promoters with high transcriptional activity increases the exogenous gene transcriptional level and enables specific expression of the recombinant proteins in seeds; 2) codon optimization of target genes with rice preferred codons can avoid rare codons to cause mRNA instability and potential intron splice sites that could improve the recombinant protein expression at the translational level; 3) selection of specific 5' and 3' UTRs can enhance translation initiation and mRNA stability; 4) using specific protein sorting signals to locate the recombinant protein in a specific subcellular vacuole not only increase the expression level of the recombinant protein, but also facilitates the downstream isolation and purification. In particular, the selection of stronger promoters is most effective, such as the use of rice endosperm-specific and stronger promoters Gil and Gt13a, etc. For example, the transcription activity of Gt13α promoter is higher at least 48.8% over Ga (Ning, et al. 2008, Oral administration of recombinant human granulocyte macrophage colony stimulating factor expressed in rice endosperm can increase leukocytes in mice. Biotechnol Lett. 30:1679-1686).

Patents ZL200510019084.4 and ZL200610019285.9 describe the use of the rice storage protein Gt13α promoter. Although the Gt13α promoter is the most transcriptionally active promoter among 13 rice storage glutenin genes encoding rice in nature (Kusaba et al., (2003) Low glutelin content1: a dominant mutation that suppresses the glutelin multigene family via RNA silencing in rice. Plant Cell 15:1455-1467), the yield of recombinant human serum albumin in rice endosperm cells reached up to 2.75 g/kg brown rice (He et al., (2011) Large-scale production of functional human serum albumin from transgenic rice seeds, Proc. Natl. Acad. Sci. USA 2011. vol. 108 (47): 19078-19083). For further increase the expression of the recombinant protein in rice endosperm cell, it is difficult find a stronger promoter than Gt13α promoter in nature due to Gt13α promoter is the strongest promoter in the rice storage protein gene. Therefore, there is a need to artificially create a promoter with higher transcriptional activity than that of Gt13α to drive higher expression of the recombinant protein in rice endosperm cells.

SUMMARY OF THE INVENTION

An object of the present invention provides an artificially modified endosperm-specific promoter EnhGt13α (Enhanced Gt13a) and use thereof for further enhance of the expression of recombinant proteins in rice endosperm cells. Several transcriptional cis-acting elements that negatively regulates the expression (repressor) are removed and the new cis-acting elements that positively regulates the expression (an enhancer or enhancer of the TATA cassette and a matrix attachment region (MAR), etc.) are generated by site-directed mutation on the cis-acting element in Gt13α (Os01g0762500, EU264102). The increasing the transcriptional activity of the promoter tested by transient GUS gene expression and further increasing the expression of the exogenous proteins are approved in rice endosperm.

The Present Invention Provides the Following Technical Solutions

A modified plant endosperm-specific promoter having a nucleotide sequence as shown in any one of the sequences SEQ ID NO. 1 to SEQ ID NO. 5; and specifically, having the nucleotide sequence as follows:

1) having the DNA sequence as shown in SEQ ID NO. 1; the sequence is a Gt13aΔ281bp truncated promoter by a deletion of 281 bases at the 5' end of the Gt13α promoter (as shown in SEQ ID NO. 6); or
2) having the DNA sequence as shown in SEQ ID NO. 2; the sequence is an artificially modified AT-rich promoter by the DNA sequence as shown in SEQ ID NO. 1 with site-directed G→T mutations at positions 322, 708 and 712 and a site-directed G→A mutation at position 733; or
3) having the DNA sequence as shown in SEQ ID NO. 3; the sequence is a new candidate promoter Gt13aΔ281+ CAAT motif as shown in SEQ ID NO. 1 with a CC to TT mutation at position 620 to produce a new CAAT and an insertion of the sequence TACAAAT-GATGTGTCAATTACA at position 340 to produce three repeats of CAAT elements; or 4) having the DNA sequence as shown in SEQ ID NO. 4; the sequence is a DEL new candidate promoter as shown in SEQ ID NO. 1 with a deletion of AAGT-CATAACTGAT motif at positions 301-322, a deletion of CAGTG element at position 555 and a GAAAG to CAATT mutation at position 708; or
5) having the DNA sequence as shown in SEQ ID NO. 5; the sequence is a new GCN4 element-rich candidate promoter as shown in SEQ ID NO. 1 with an insertion of the sequence ATATATCATGAGTCACTTCAT and AACAAACTCTATCTT AACATT at position 808 and 841, respectively, to increase two GCN4 elements.

Preferably, the new plant endosperm-specific promoter of the present invention has a nucleotide sequence as shown in SEQ ID NO. 1 or SEQ ID NO. 2 of the sequence listing. The most preferred promoter has the nucleotide sequence as shown in SEQ ID NO. 2.

According to the present invention, the new plant endosperm-specific promoter is fused to a genes encoded the pharmaceutical or industrial proteins or polypeptide gene, a structural gene, a regulatory gene, an antisense gene of a structural gene, an antisense gene of a regulatory gene for driving the expression of a structural gene, a regulatory gene, an antisense gene of a structural gene and an antisense gene of a regulatory gene, a gene regulating a metabolite, an antisense gene of a gene regulating a metabolite.

The present invention also provides an expression cassette comprising any one of the above plant endosperm-specific promoters.

The present invention also provides a recombinant expression vector comprising any one of the above plant endosperm-specific promoters.

The recombinant protein expression vector is a recombinant protein expression vector constructed by containing the above expression cassette within a plasmid and a delivery vector. The recombinant protein expression vector is a recombinant protein plant expression vector, and the recombinant protein expression vector comprises the above expression cassette and is capable of transforming the expression cassette into a plant host cell, tissue or organ and its progeny has the capable of integrating it into the genome of the host.

The recombinant protein expression vector can be transformed into a plant cell, tissue or organ using conventional gene transformation approaches such as Ti plasmid, Ri plasmid, plant virus vector, direct DNA transformation, microinjection, *Agrobacterium* mediation or gene gun, to obtain a genetically engineered the transgenic plant cell, tissue, or organ, as well as a complete plant and its clones or offspring that differentiate and regenerate from this.

The present invention also provides a host bacterium comprising any one of the above plant endosperm-specific promoters.

The present invention also provides a genetically engineered plant cell line, or transgenic plant or cell line comprising one above endosperm-specific promoters.

The present invention also provides the above plant endosperm-specific promoter in the preparation of a genetically engineered or transgenic plant and use thereof.

The present invention also provides the use thereof the above plant endosperm-specific promoter in a genetically engineered or transgenic plant expressing any recombinant proteins or metabolites.

The method of breeding a plant endosperm-specific expression of exogenous genes by using the above plant endosperm-specific promoter also falls within the scope of the present invention.

The method of breeding a plant with endosperm-specific expression of exogenous genes comprises transforming a plant expression vector into the plant to screen for a transgenic plant that specifically express the exogenous genes in the endosperm.

Any transgenic plant mentioned above is a monocotyledonous plant or a dicotyledonous plant. The monocotyledonous plant may be a graminaceous plant, such as rice, wheat, corn, barley, chestnut, sorghum or oats etc; the dicotyledonous plant may be soybean, rape or sunflower etc.

The present invention also provides a method of producing a recombinant protein using the plant endosperm-specific promoter of claim 1, the method comprises of:
1) constructing a rice endosperm-specific intermediate vector using the plant endosperm-specific promoter of claim 1;
2) synthesizing the recombinant protein gene;
3) operably ligating the vector of step 1) with the gene of step 2), to obtain a vector for recombinant protein expression driven by the promoter;
4) transforming a plant with the expression vector of step 3) and expressing the recombinant protein in the endosperm;
5) extracting and purifying the recombinant protein from the plant.

In a specific embodiment of the present invention, provided is a method of preparing a recombinant feline serum albumin (FSA), the gene of FSA has the nucleotide sequence as shown in SEQ ID NO. 7.

Compared to Gt13α promoter, the beneficial effects of the modified promoter of the present invention are reflected in that:
1) a new promoter sequence is obtained by deletion of Gt13a, which increases the transcriptional activity of the 0-glucosidase (GUS) gene by 7.2% compared to the unmodified promoter;
2) The new promoter, designated as EnhGt13a, obtained by the mutation of the core region of cis-elements at deletion version of Gt13a, increases 28.52% of the relative GUS activity compared to Gt13α promoter using the rice immature endosperm transient GUS expression system in vitro;
3) the EnhGt13α promoter of the present invention drives stable expression of exogenous genes, the level of exogenous recombinant protein, FSA, in the endosperm bioreactor was significantly increased 46.57% compared to unmodified Gt13α promoter.
4) the EnhGt13α promoter of the present invention driven GUS reporter gene expression in rice endosperm is suitable for all endosperm seeds plants, especially for breeding genetically engineered rice varieties expressing pharmaceutical proteins;
5) the EnhGt13α promoter of the present invention can significantly improve the expression and accumulation of exogenous protein in endosperm, which made the foundation for researches of improving seed quality and molecular pharming using biotechnology, which has wide application prospectives.

DETAILED DESCRIPTION OF THE INVENTION

Figure 1:
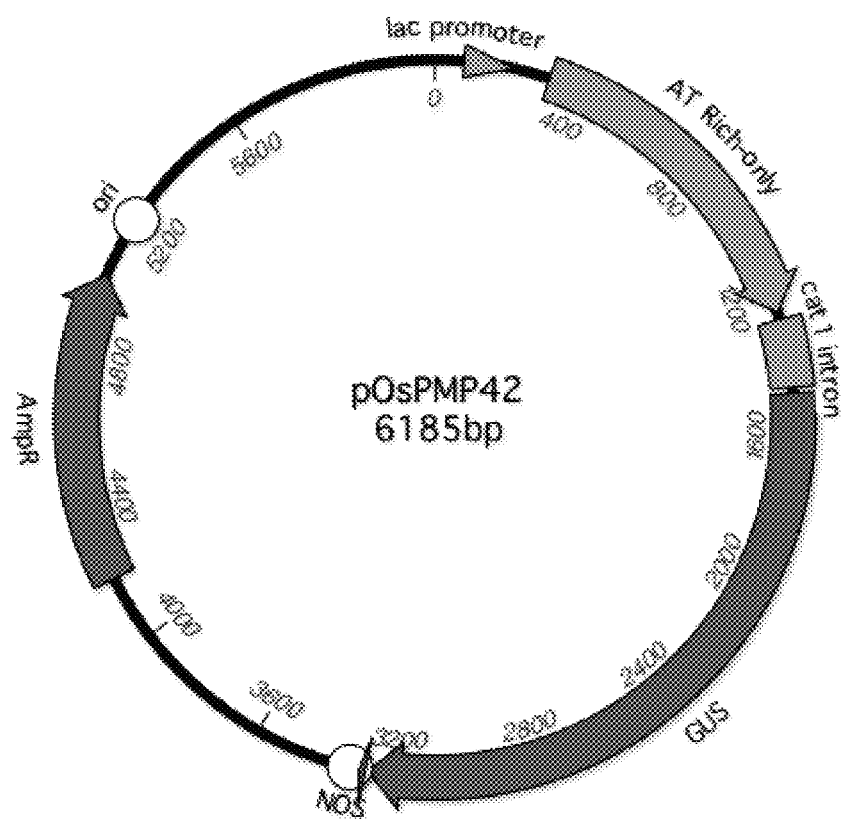
FIG. 1. Schematic diagram of the structure of the vector, pOsPMP42, driven GUS expression.

The technical proposals of the present invention will be described in detail below by the examples and figure data in order to better understand the advantages of the present invention. The examples provided should be interpreted as illustrative examples of the method of the present invention, while it do not means in any way to limit the technical proposals and scope of protection revealed by the present invention.

Experimental Materials

Vector pOsPMP42, vector pOsPMP002: prepared according to Ning, et al. 2008, Biotechnol Lett. 30:1679-1686
Gold microcarriers: Cat. No: 1652263, BioRad, Inc.
pBI221 vector: Clontech, Inc., USA
pUC57 vector: GenScript Biotech Corporation
*E. coli* strain DH5α: Cat. No: 9057, Takara Corporation
*Agrobacterium* plasmid pCAMBIA1300: Cat. No:HG-VZC0323, CAMBIA (Australia)
Rice (*Oryza sativa*): Variety 9-2-5
*Agrobacterium* EHA105: Cat. No:MF2302-1000UL, MKBio Inc.
Gene gun PDS-1000/He: BioRad Inc.
Microplate reader: spectrophotometer, Varioskan, Thermo Scientific Inc.

[Example 1] Cloning, Sequencing and Bioinformatics Analysis of Rice Endosperm Promoter GT13α

1. Site-Directed Mutation of the Rice Endosperm-Specific Promoter GT13a

The bioinformatics analysis of the rice endosperm Gt13α promoter sequence was conducted using PLANTCARE, an online analysis tool for plant cis-acting elements (at http://bioinformatics.psb.ugent.be/webtools/plantcare/html). The results showed that the rice endosperm Gt13α promoter has endosperm-specific regulatory elements, such as AACA-motif, CAAT-box and GCN4-motif. Five artificially modified promoter sequences were designed by the present invention as shown in Table 1.

TABLE 1

| Artificially modified Gt13a promoter | | |
|---|---|---|
| SEQ ID No. | Modified promoter | Modification site |
| 1 | Gt13aΔ281 bp | Gt13aΔ1 to 281 |
| 2 | Gt13aΔ 281 bp + AT | Gt13aΔ281 bp, G→T at positions 322, 708 and 712; G→A at position 736. |
| 3 | Gt13aΔ 281 + CAAT | Gt13aΔ281 bp, CC to TT mutation at position 620, to generate a new CAAT; TACAAATGATGTGTCAATTACA sequence inserted at position 340, to generate three CAAT repeat elements. |
| 4 | Gt13aΔ 281/Del | Gt13aΔ281 bp, AAGTCATAACTGAT motif at positions 301-302 was deleted; a CAGTG element at position 526 was deleted; GAAAG to CAATT at position 708 was mutated |
| 5 | Gt13aΔ | Gt13aΔ281 bp, ATATCATGAGTC ACTTCAT sequence was inserted at position 808; AACAAACTCTATCTTAACATT sequence was inserted at position 841; two GCN4 elements were added |
| 6 | Gt13a (CK) | Unmodified promoter, as control |

In Table 1:
Promoter Gt13aΔ281 bp (SEQ ID No. 1) was obtained by deletion of 281 bp at the 5' end of the promoter Gt13a, wherein it comprises 2 cis-acting elements of the negative transcriptional regulator WRKY;
Promoter Gt13aΔ281 bp + AT (SEQ ID No. 2) was obtained based on SEQ ID No. 1, with the G→T at positions 322, 708 and 712; the G→A at position 733; to generate a new matrix binding region as well as a TATA BOX5 (TTATTT); the point mutation at position 710 to generate a transcriptional activator cis-acting element TAAAG; and the point mutations at positions 701 and 706 to create a TATA BOX sequence;
Promoter Gt13aΔ281 + CAAT (SEQ ID No. 3) was obtained based on SEQ ID No. 1, with the CC to TT mutation at position 620 to generate a new CAAT, and the TACAAATGATGTGTCAATTACA sequence inserted at position 340 to generate three CAAT repeat elements;
Promoter Gt13aΔ281/Del (SEQ ID No. 4) was obtained based on SEQ ID No. 1, with the AAGTCAT AACTGAT motif at positions 301-322 was deleted; the CAGTG element at position 526 was deleted; and the GAAAG to CAATT mutation at position 708.
Promoter Gt13aΔ (SEQ ID No 5) was obtained based on SEQ ID No. 1, with the ATATATCATGAGTCACTTC AT sequence was inserted at position 808; the AACAAACTCTATCTTAACATT sequence was inserted at position 841 to create two GCN4 elements.

The artificially modified promoter sequences were synthesized by GenScript Biotech Corporation. The synthesized sequences were ligated to a GUS expression vector to produce a series of GUS gene expression plasmids driven by different artificially modified promoters. FIG. 1 shows the structure of one of the vectors, pOsPMP42.

[Example 2] Detection of GUS Transcriptional Activity of the Artificial Promoters In order to detect whether the artificially modified promoters enhance the transcriptional activity in endosperm, immature rice endosperm cells as a transient expression system were used. The GUS transient expression vector drived by artificially modified promoters were constructed. The transcriptional activity of the promoters was detected by GUS transient expression in immature rice endosperm cells in vitro. The main steps were as follows:

1. Pre-Treatment of Gold Microcarriers
1) 50 mg of gold microcarriers with a diameter of 1 μm was weighed and placed in a 1.5 ml centrifuge tube;
2) 1 ml of anhydrous ethanol was added;

3) Subjected to ultrasonic treatment in ice bath for 2 min with 30 s intervals after each 30 s of ultrasound treatment;
4) Centrifuged at less than 4000 rpm for 1 sec, then the supernatant was aspirated;
5) 1 ml of sterile water was added and subjected to ultrasonic treatment in an ice bath for 2 min, and then the supernatant was removed, by repeating steps 3 and 4;
6) Step 5) was repeated once;
7) 1 ml of sterile water was added and subjected to ultrasonic treatment in an ice bath, and re-suspended for use (50 mg/ml gold microcarriers suspension).

2. Coating with Vector DNA
1) Take 50 µl of gold microcarriers suspension solution;
2) add 30 µl (2 µg/µl) of plasmid DNA containing 15 µg GUS plasmid DNA and 15 µg LUC plasmid DNA;
3) 50 µl of 2.5M calcium chloride was slowly dropwise added with vortexing;
4) 20 µl of 0.1 M spermidine was slowly dropwise added with vortexing;
5) They were mixed well by vortexing for 10 minutes with 1 min intervals;
6) The supernatant was removed;
7) Add 50 µl of anhydrous ethanol to re-suspend the gold microcarriers at the bottom of the tube;
8) Add another 500 µl of anhydrous ethanol to wash the coated gold particles;
9) After brief centrifugation and remove the supernatant, it was re-suspended by 40 µl of anhydrous ethanol for immediately use.
10) Take 12 µl resuspendant and add to the center of the sterilized carrier membrane.

3. GUS Transient Expression in Immature Rice Endosperm Cells by Gene Bombardment
1) Separation of immature rice endosperm. Rice panicle after 7-10 days flowering were taken, sterilized with 70% alcohol for 1 min, sterilized with 20% sodium hypochlorite for 15 min, rinsed 5 times with sterile water and placed in sterile water for use.
2) An appropriate amount of TAIB (complete medium supplemented with 20 mM $NH_4NO_3$, 100 µg/ml Cefotaxime, 100 µg/ml Timentin) medium was placed on petri dishes with two layers of filter paper. A scalpel was used to cut at the immature rice embryos and then the complete immature endosperms were gently squeezed out and placed in the center of the medium containing TAIB, with about 15 immature endosperms in each dish.
3) The PDS-1000/He gene gun was used transformation according to the manufacturer's instructions.
4) The bombardment immature endosperms were incubated at 25° C. overnight.

4. Qualitative Analysis of GUS Staining
To test the viability of the GUS transient expression system in immature rice endosperm, transformed immature endosperm was incubated at 25° C. for 18-24 h. The medium fluid in the dishes was aspirated and 2 ml of GUS staining solution was added directly to the endosperms. Observation and photographed after 2-10 h of color development at 37° C.

5. Quantitative GUS Assay of Relative Transcriptional Activity Mediated by the Endosperm-Specific Promoters
1) The bombarded immature endosperms were incubated at 25° C. for 24 h. The endosperms were transferred to a centrifuge tube, ground and extracted with 55 µl of extraction solution (Luciferase Cell Culture Lysis Reagent, 1×, Promega Ltd, USA, Cat no. E1500), and centrifuged at 13,000 rpm for 5 min. 20 µl of each supernatant sample was dispensed into 96-well ELISA plates for the detection of GUS and LUC activity, respectively.
2) Quantitative assay of LUC: 100 µl of reaction solution (luciferase detection reagent, Promega Ltd., USA, Cat no. E1500) was added to the extratant and incubated at 25° C. for 25 min. And the samples were detected by chemiluminescence method using a microplate reader to obtain the LUC activity.
3) Quantitative assay of GUS: 10 µl of 4-MUG (2 mmol/L) was added to sample and incubated at 37° C. for 1 hour. And then the reaction was terminated by the termination solution (200 mM $Na_2CO_3$). The fluorescence value was measured at 445 nm for emission light and 365 nm for excitation light using a microplate reader. The GUS activity value of each sample was obtained. Based on the LUC and GUS activity values measured in 2 and 3 steps, the relative GUS gene enzyme activity was calculated.

Figure 2:
FIG. 2. Staining image of GUS transient expression in immature rice endosperm expressing.
Figure 3:
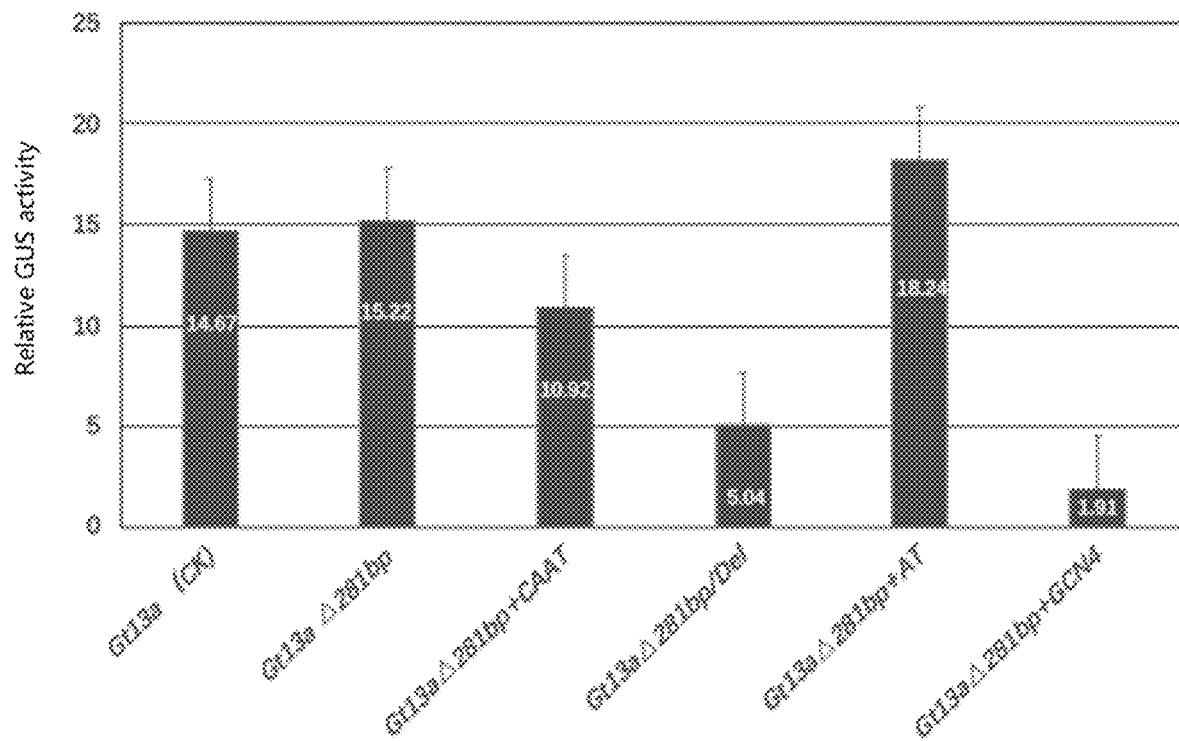
FIG. 3. Comparative diagram of relative GUS activity mediated by the artificially modified promoters.

6. Experimental Results
1) To test whether the transient expression system of immature rice endosperm was working, GUS staining was performed on the transformed immature endosperm mediated by bombardment. The results showed that all immature rice endosperm cells could be stained by GUS staining solution, indicating that the transient expression system of immature rice endosperm was working properly (FIG. 2).
2) The relative GUS activity assay for five modified endosperm-specific promoters in immature rice endosperm cells was examined using the Gt13α promoter as control. The results showed that the relative GUS activity of the promoter with 281 bp deleted at the 5' end (Gt13αΔ281) was increased by 7.27% compared to the control Gt13α promoter. The relative GUS activity of the promoter with site-directed mutations in the core region of transcriptional activity (Gt13αΔ281+AT) was increased by 28.53%, reaching a significant level (P<0.05), compared to the control Gt13α promoter. The relative GUS activity of Gt13αΔ281+CAAT was reduced by 23.08% compared to the Gt13α promoter. The relative GUS activity of Gt13αΔ281+DEL was reduced by 64.49% compared to the Gt13α promoter. The relative GUS activity of Gt13αΔ281+GCN4 was reduced by 86.53% compared to the Gt13α promoter (FIG. 3). The results showed that the promoter with the deletion of two negative regulatory cis-acting elements at the 5' end of the Gt13α promoter (Gt13αΔ281) and the promoter with site-directed mutations of AT in the core transcriptional regulatory region (Gt13αΔ281+AT) can significantly increase the transcriptional activity in immature endosperm transient expression system.

[Example 3] Functional Analysis of Mutation Sites

To reveal whether the create new cis elements after deletion and site-directed mutations generate, the two artificially modified promoter cis-acting elements with significantly increased transcriptional activity were analyzed using PLACECARE promoter analysis software.

The analysis results of the cis-acting element of Gt13αΔ281 bp (SEQ ID No. 1) showed that the deleted 281 bp at the 5' end of Gt13α contained 2 cis-acting elements of the transcriptional negative regulator WRKY (see Table 2).

The removal of the 2 transcriptional negative regulator WRKY motifs from Gt13αΔ281 bp resulted in a 7.2% increase in relative GUS activity over Gt13α promoter.

TABLE 2

Analysis of cis-acting elements of Gt13aΔ281 bp

| Factor or site name | Loc. (Str.) | Signal sequence | Signal sequence | Functional definition | Reference |
|---|---|---|---|---|---|
| WRKY71OS | 70(+) | TGAC | S000447 | Negative regulator | Plant Physiol. |
| WRKY71OS | 77(-) | TGAC | S000447 | Negative regulator | 134:1500-1513(2004) |

Analysis of point mutation of Gt13αΔ281bp+AT (SEQ ID No. 2) showed that multiple positive transcriptional regulatory cis-acting elements were generated by the site-directed AT mutations, i.e., site-directed point mutations of AT at positions 701 and 706, 1) eliminated a transcriptional repressor of the AAGAA motif (Intnatl Rev Cyto Vol 119:57-96); 2) generated a new nuclear matrix attachment region (Matrix Attachment Region, Plant Journal, 21, 281-288) and a TATA BOX5 (TTATTT); 3) added a TATA box sequence; 4) the point mutation at position 710 generated a transcriptional activator cis-acting element TAAAG; the point mutation at position 317 generated anew cis-acting element with increased tissue specificity CAAT BOX1 and a DPBF CORE DCDC3 transcriptional activator ZIP binding factor (Table 3).

The expression intermediate vector was constructed using EnhGt13α promoter. The 930 bp DNA fragment of EnhGt13α promoter with the Gt13α signal peptide were cloned into the pBI221 vector to produce an intermediate plasmid, which was then introduced into the *E. coli* strain DH5a to construct a rice endosperm-specific intermediate vector strain named pOsPMP862.

The amino acid sequence (SEQ ID NO. 8) of the mature feline serum albumin gene (Gene Bank registration number NP_001009961.1) was obtained from the National Center for Biotechnology Information (NCBI) Gene Bank, and the amino acid sequence of the FSA gene was converted into a nucleotide sequence and optimized using the rice preferred genetic codon as shown a synthetic FSA gene (SEQ ID NO. 7). In the artificial synthesis of FSA gene, restriction endonucleases MlyI and XhoI sites were added to both ends of the gene and then cloned into pUC57 vector (Kingsray Biosciences Ltd.) designated pOsPMP850.

Figure 4:
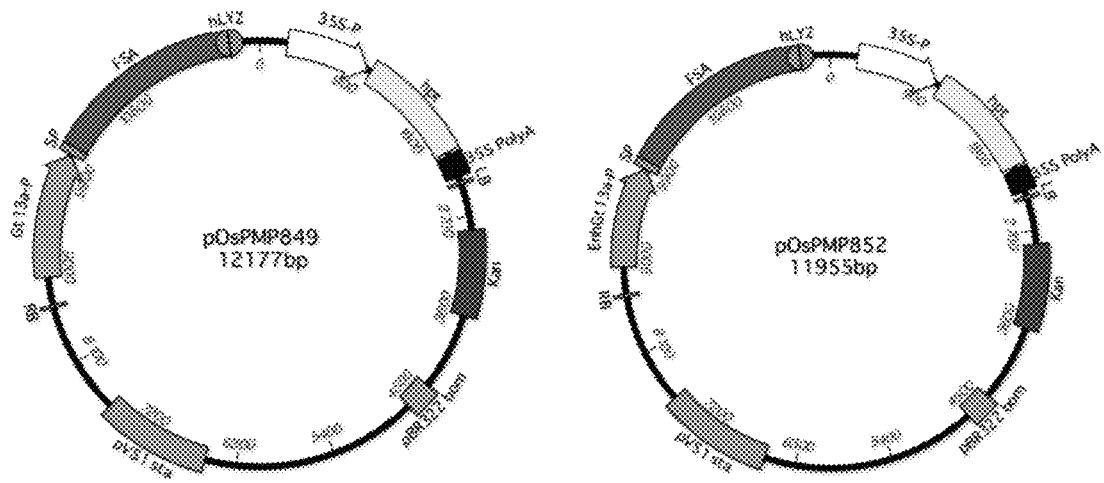
FIG. 4. Schematic diagram of the structures of rice endosperm-specific expression vectors, pOsPMP849 and pOsPMP852.

To construct Gt13α-mediated FSA expression vector, pOsPMP850 DNA was digested by MlyI and XhoI to obtain synthetic FSA gene, and then ligated to the pOsPMP002 intermediate vector digested by NaeI and XhoI designated as pOsPMP848; pOsPMP848 was digested with HindIII and EcoRI to obtain the entire expression cassette and ligated to the same enzymatic sites of the *Agrobacterium* plasmid pCAMBIA1300, to generate the vector designated as pOsPMP849 (FIG. 4).

To construct EnhGt13α mediated expression vector, pOsPMP 850 plasmid DNA was digested with MyII and XhoI to obtain FSA DNA fragment. And then ligated to plasmaid pOsPMP862 that digested by NaeI and XhoI. The

TABLE 3

Analysis of cis-acting elements of Gt13aΔ281 bp + AT

| Factor or site name | Loc. (Str.) | Signal sequence | Signal sequence | Functional definition |
|---|---|---|---|---|
| CAAT BOX1 | 317(+) | CAAT | S000028 | increase tissue specificity |
| DPBF CORE DCDC3 | 329(+) | ACACNNG | S000292 | ZIP binding sites |
| -300 ELEMENT | 701(+) | TGHAAARK | S000122 | AAGAA repressor cis-element |
| TATA BOX5 | 705(-) | TTATTT | S000203 | the generated TATA box |
| MARA BOX1 | 706(+) | AATAAAYAAA | S000063 | add a nuclear matrix attachment region MAR |
| TAAAG STKST1 | 712(+) | TAAAG | S000387 | transcription activator cis-acting element |

Therefore, the promoter Gt13αΔ281+AT in the present invention significantly enhanced gene expression, designated this promoter as EnhGt13α (Enhanced Gt13α).

[Example 4] Application of EnhGt13α Promoter

To confirm the effect of the improve recombinant protein expression in endosperm using EnhGt13α in rice endosperm cells, Two expression vectors containing feline serum albumin (FSA) gene mediated by Gt13α and EnhGt13α, respectively, were constructed, which were used to confirm whether EnhGt13α promoter could enhance the expression of feline serum albumin in rice endosperm cells.

1. Construction of an Expression Vector resulting plasmid designated as pOsPMP851. The pOsPMP851 plasmaid DNA was digested with HindIII and EcoRI to obtain entire expression cassete DNA fragment and then ligated to plasmid pCAMBIA1300, an *agrobacterium* plasmid, digested with the same enzymes. The resulting plasmid was designated as pOsPMP852 (FIG. 4).

The pOsPMP849 and pOsPMP852 vectors were transferred into *Agrobacterium* EHA105, respectively, for *Agrobacterium*-mediated genetic transformation.

2. *Agrobacterium*-mediated genetic transformation process 2.1 Calli Induction

1) Mature rice seeds were husked and sterilized by soaking in 70% alcohol for 1 min and treated with 20% sodium hypochlorite for a further 30 min;

2) Washed with sterile water for 5-7 times;
3) The sterilized seeds were inoculated onto induction medium ($N_6$ medium), with 6-8 seeds in each dish;
4) Subjected to light treatment at 32° C. for about 5-7 days.

2.2 Agrobacterium Preparation

*Agrobacterium* containing the plasmids pOsPMP849 and pOsPMP852, respectively, were cultured in flat dish containing median with Caramycin at 28° C. for 2-3 days.

2.3 Single colony of *Agrobacterium* were picked into suspension medium (AAM liquid medium) using an inoculation loop and incubated at 28° C. with shaking (160 rpm). Generally 100 ml of medium can be scraped into 3 to 4 loops with the inoculation loop.

2.4 Agrobacterium Infection (Co-Incubation)
1) The calli tissue was transferred to sterilized triangular flasks;
2) The $OD_{600}$ value of *Agrobacterium* suspension was adjusted to between 0.05 and 0.1;
3) The calli were suspended in AAM medium and incubated for 1.5 min with continuous shaking;
4) The *agrobacterium* solution was discarded, the excess solution was blotted up on the sterile filter paper and the calli tissue was placed on the sterile filter paper to drain for 30-45 min;
5) The sterile filter paper was placed on $2N_6$-AS medium. Then 500 μl of AAM containing AS (acetosyringone, 250 mg/ml) was dropped onto sterile filter paper, and the infected calli were placed on the filter paper and co-cultured for 3 days at 25° C. in the dark.

2.5 Water Washing and Screening
1) calli tissues were transferred to sterile triangular flasks;
2) The calli tissues were washed with sterile water for 5-7 times;
3) The infected calli tissues were soaked in sterile water containing 0.5 g/L of cephalexin for about 30 min, followed by shaking 180-200 RPM at 28° C. for 20-30 min;
4) The sterile water containing antibiotics was poured off and the triangular flasks were placed upside down in a sterile petri dish containing filter paper for about 15 min;
5) The calli tissues were dried on the sterile filter paper;
6) The calli tissues were transferred to a selective medium containing HPT antibiotics for 20-30 days.

2.6 Calli Tissue Differentiation

After selection for 20-30 days, the calli tissues with HPT resistance were transferred to a differentiation medium ($N_6$ medium) and incubated in the light at 26° C. for 20-30 days.

2.7 Rooting

After 20-30 days differentiation, the differentiated plantlet from the differentiation medium were transferred to a medium containing ½ MS to incubate at 28° C. under light for 30 days to rooting and transferred to the field for growth.

3. Identification and Planting of Genetically Engineered Seedlings 3.1 Extraction of Genomic DNA
1) About 2 cm of leaves from TO generation HPT-positive plants were put into the tubes, added 600 μl CTAB extraction buffer (2% CTAB, 1.38 M NaCl, 0.1 M Tris-HCl, 20 mM EDTA, pH 8.0), grinded in a vibrator crusher, then incubated in a 65° C. water bath for 60 min. An equal volume of chloroform/isoamyl alcohol was added, and mixed gently with invert, and the centrifuged at 12000 rpm for 10 min. The supernatant was transferred to a new 1.5 ml centrifuge tube, an equal volume of isopropanol was added, mixed gently with invert. After incubation at room temperature for 60 min, the material was centrifuged at 12000 rpm for 10 min. The supernatant was removed and the DNA precipitate was rinsed in pre-cooled 70% ethanol, air-dried. Then the DNA was dissolved in 80 μl of TE buffer and stored at −20° C. for use.

2) PCR Amplification

Genomic DNA was extracted from the leaves of the genetically engineered plants were identified by PCR using FSA-specific primers (forward primer sequence as shown in SEQ ID No. 9: AGCTACCAGGGCAACAGCGA; reverse primer sequence as shown in SEQ ID No. 10: ATCTCGTAGAGGTACTTGCCGA). The PCR assay was performed as follows:
1) 1 μl of rice genomic DNA was used as template and positive (plasmid DNA) and negative (sterile water) controls were provided.
2) PCR amplification reaction comprised 2.5 μl of 10×Buffer, 0.15 μl of 5 U/μl rTaqase, 4 μl of 2.5 mM dNTP, 0.5 μl each of forward and reverse primers; added with $ddH_2O$ to 25 μl.
3) Pre-denaturation at 94° C. for 5 min, followed by 35 cycles of denaturation at 94° C. for 30 s, annealing at 55° C. for 30 s and extension at 72° C. for 40 s, and a final extension at 72° C. for 10 min.
4) The PCR amplification product was electrophoresed in 1% agarose gel, stained with EB. The PCR results were observed in a gel imager.

4. Determination of Expression Levels

The T1 generation seeds produced from the TO plants were harvested for FSA protein assay, the specific steps as follows:
1) Extraction of crude endosperm protein: 5 grains were husked (about 77 mg of brown rice), ground into rice flour, and extracted with 1 ml of extraction solution (50 mM Tris, 150 mM NaCl, pH 7.5) at room temperature for 60 min, then centrifuged at 13000 rpm for 5 min. The supernatant was used for SDS-PAGE analysis.
2) SDS-PAGE analysis: 50 μl of crude extract or 5 μg of FSA standard protein was added with 10 μl of sample buffer, denatured at 100° C. for 5 min. 10 μl of each sample was loaded onto 10% polypropylene gel denaturing gel and electrophoresed at 160 V for 45 min. And then stained with 0.1 mg/ml Komas Brilliant Blue, decolorized, and then photographed.
3) Semi-quantitative analysis of recombinant FSA expression. The FSA expression of each line was analyzed semi-quantitatively based on the grey scale of the known content of FSA in the same SDS-PAGE gel. The FSA protein content of each line was calculated according to the grey scale.

5. Results and Analysis

1) Identification of Target Gene Positive Plants

Figure 5:
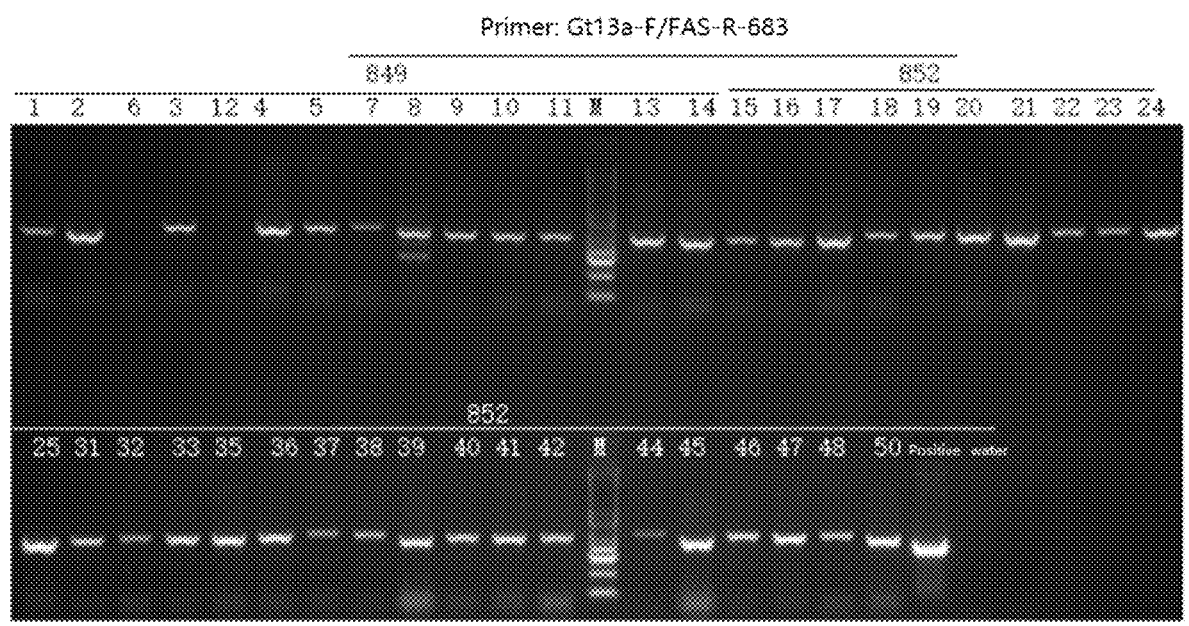
FIG. 5. Electropherogram of PCR products of target genes in TO generation plants.

Using the promoter region specific sequence as the forward primer (as shown in SEQ ID No. 9) and FSA gene specific sequence as the reverse primer (as shown in SEQ ID No. 10), 14 target gene positive TO plants of pOsPMP849 (Gt13α promoter) and 36 target gene positive plants of pOsPMP852 (EnhGt13α) were obtained by PCR (FIG. 5). These plants were grown up to maturity, of which a total of 10 plants of pOsPMP849 produced seeds; and a total of 20 plants of pOsPMP852 produced seeds.

2) Semi-Quantitative Analysis of FSA Expression

Figure 6:
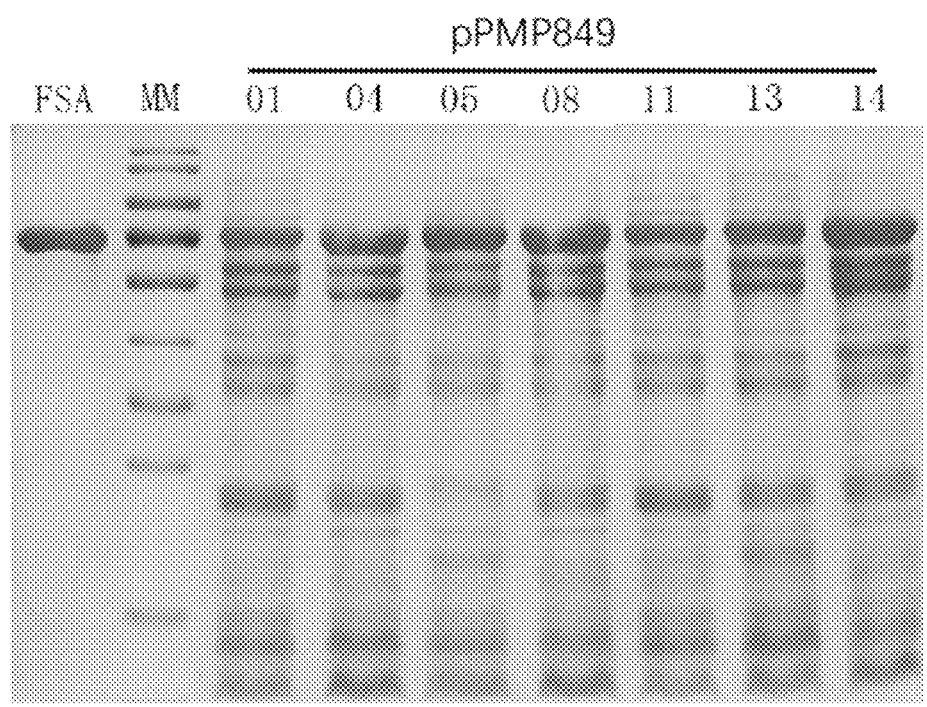
FIG. 6. A SDS-PAGE for FSA protein extracted from TO generation seeds using pOsPMP849.
Figure 7:
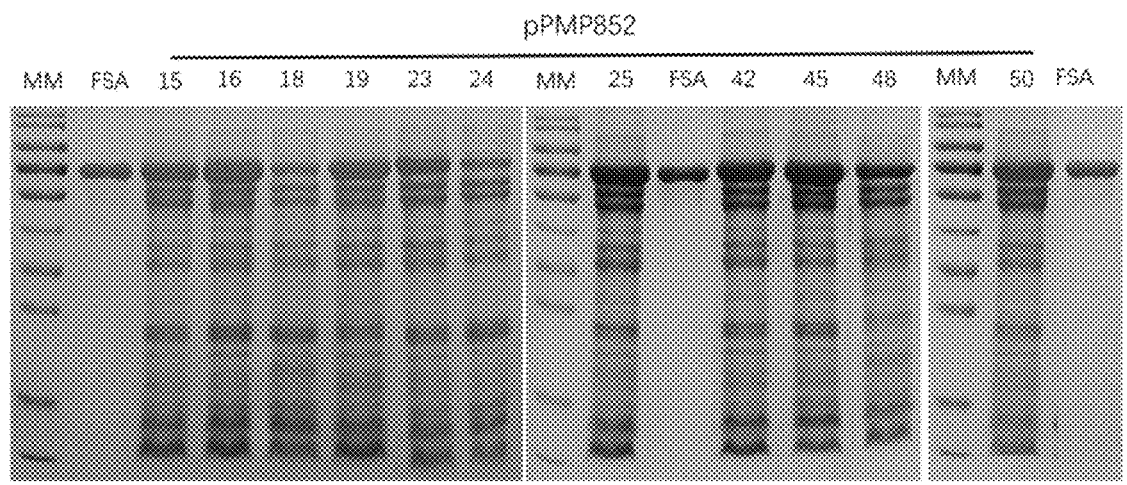
FIG. 7. A SDS-PAGE of FSA protein extracted from TO generation seeds using pOsPMP852.
Figure 8:
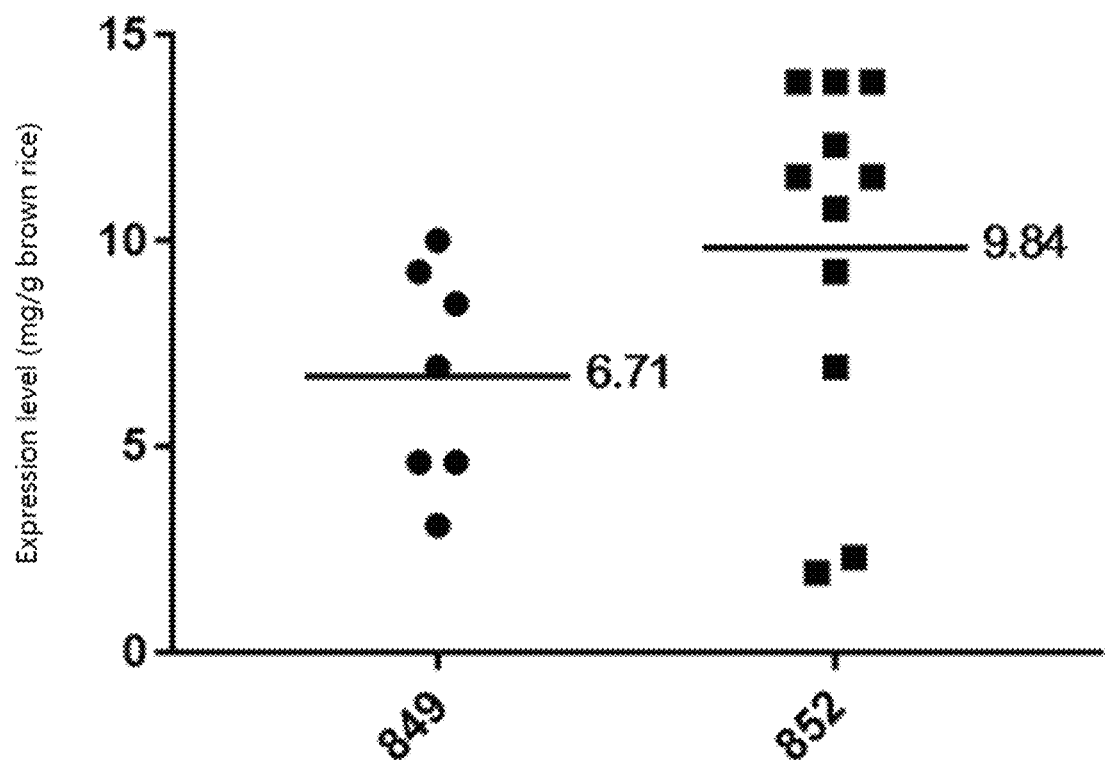
FIG. 8. Comparative diagram of FSA expression levels in rice endosperm driven by Gt13α and EnhGt13α promoters.

To roughly estimate the FSA expression of each strain, grey scale comparison was performed using the same PAGE gel with known concentration of FSA as a reference, and the expression level of FSA was estimated based on the grey scale. Among them, 7 lines of pOsPMP849 expressed FSA (FIG. 6); and 11 strains of pOsPMP852 expressed FSA (FIG. 7) were analyzed. The results are shown in FIG. 8. The FSA expression level of pOsPMP849 ranged from 3.08-10.01 mg/g brown rice with an average of 6.71 mg/g brown rice; the FSA expression of pOsPMP852 ranged from 2.31-13.86 mg/g brown rice with an average of 9.84 mg/g brown rice. The EnhGt13α promoter mediated FSA expression increased 3.13 mg/g brown rice, counting for 46.57% higher than that of Gt13α promoter mediated FSA expression. The results showed that the EnhGt13α promoter can significantly increase the expression of recombinant protein in rice endosperm.

In summary, there are various cis-acting elements in the promoter region, such as enhancer that enhance transcription and repressor that block transcription. These cis-acting elements interact with trans-acting factors to regulate the spatial- and temporal-expression of genes and also the level of expression as well. Usually, trans-acting factors regulate gene transcription positively or negatively through these cis-acting elements. The introduction of a nuclear matrix attachment region in the promoter region also significantly enhances the entry of RNA synthase into the promoter region thereby increasing transcriptional activity. The present invention is obtains a new promoter EnhGt13α with stronger transcriptional activity than the natural endosperm-specific promoter Gt13α was obtained by site-directed mutation of the key cis-acting elements of Gt13α promoter, either by removing the cis-acting elements that negatively regulate transcription or by generating new cis-acting elements that positively regulate transcription and nuclear matrix attachment regions. The relative GUS activity of the endosperm-specific promoter EnhGt13α was 28.52% higher than that of Gt13α in vitro rice immature endosperm transient expression system. The expression of recombinant feline serum albumin (FSA) mediated by EnhGt13α promoter reached 9.84 mg/g brown rice, an increase of 46.57% over Gt13α-mediated FSA of 6.71 mg/kg brown rice.

The results show that the EnhGt13α promoter in the present invention mediates the expression of β-glucosidase (GUS) reporter gene in rice endosperm is therefore suitable for all plants with endosperm seeds, especially for breeding genetically engineered rice varieties expressing pharmaceutical proteins. The EnhGt13α promoter in the present invention can significantly enhance the expression and accumulation of exogenous genes in endosperm, which lays the foundation for research on improving seed quality and molecular pharming using biotechnology, and has great application prospects.

```
>Gt13aΔ281
                                                           SEQ ID NO: 1
TGAAACAATA TTATGAGTAA TGTGTGAGCA TTATGGGACC ACGAAATAAA AAAAGAACAT TTTTATGAGC

AGTGTGTTCT CAATGAGCCT TGAATGTTAT CACCCAGGAT AAGAAACCCT TAAGCAATGA AACATGCAAG

CGTTTAATGT GCAAAGTTGG CATTCTCCAC GACATAATGC AAAAGAAGAT ATAATCTATG ACATAGCAAG

TCATGCATCA TTTCATGCCT CTGTCAACCT ATTCATTTCT AGTCATCTAG GTAAGTATCT TAAGCTAAAG

TGTTAGAACT TCCCATACAT AAGTCATAAC TGATGACAAT TGGGTGTAAC ACATGACAAA CCAGAGAGTC

AAGCAAGATA AAGCAAAAGG ATGTGTACAT AAAACTACAG AGCTATATGT CATGTTGCGA AAAGAGGAGA

GCTTATAAGA CAAGCCATGA CTCAAAAAAA ATTCACATGC CTACTGTGGC CCATATATCA TGCAACAATC

CAAAAACTCA CAGGTCTCGG TGTTGATCGT GTCAACATGT GACCACCCTA AAAACTCTTC ACTAAATATT

AAAGTATTGC TAGAACAGAG CTTCAAGATA TAAGTCATGA TCACCAACAA CCATGTTCAA AAAGAAATAG

AAAGCTATGG CACAGCAACA AAAAGCAAAA GCATGCATGG ATATAATCTT TAACATCATC CATGTCATAT

TGCAAAAGAA AGAAAGAGAG AACAATACAA ATGATGTGTC AATTACACAT CCATCATTAT CCATCCACCT

TCCGTGTACC ACACTTCATA TATCATGAGT CACTTCATGT CTGGACATTA ACAAACTCTA TCTTAACATT

CAAATGCATG AGACTTTATC TCAC*TATAAA T*GCACAATGA TTTAGCATTG TTTCTCACAA AACCATTCAA

GTTCATTAGT ACTACAACAA

>Gt13aΔ281 + AT
                                                           SEQ ID NO: 2
TGAAACAATA TTATGAGTAA TGTGTGAGCA TTATGGGACC ACGAAATAAA AAAAGAACAT TTTTATGAGC

AGTGTGTTCT CAATGAGCCT TGAATGTTAT CACCCAGGAT AAGAAACCCT TAAGCAATGA AACATGCAAG

CGTTTAATGT GCAAAGTTGG CATTCTCCAC GACATAATGC AAAAGAAGAT ATAATCTATG ACATAGCAAG

TCATGCATCA TTTCATGCCT CTGTCAACCT ATTCATTTCT AGTCATCTAG GTAAGTATCT TAAGCTAAAG

TGTTAGAACT TCCCATACAT AAGTCATAAC TGATGACAAT TTGGTGTAAC ACATGACAAA CCAGAGAGTC

AAGCAAGATA AAGCAAAAGG ATGTGTACAT AAAACTACAG AGCTATATGT CATGTTGCGA AAAGAGGAGA

GCTTATAAGA CAAGCCATGA CTCAAAAAAA ATTCACATGC CTACTGTGGC CCATATATCA TGCAACAATC

CAAAAACTCA CAGGTCTCGG TGTTGATCGT GTCAACATGT GACCACCCTA AAAACTCTTC ACTAAATATT

AAAGTATTGC TAGAACAGAG CTTCAAGATA TAAGTCATGA TCACCAACAA CCATGTTCAA AAAGAAATAG
```

-continued

```
AAAGCTATGG CACAGCAACA AAAAGCAAAA GCATGCATGG ATATAATCTT TAACATCATC CATGTCATAT

TGCAAAATAA ATAAAGAGAG AACAATACAA ATGATATGTC AATTACACAT CCATCATTAT CCATCCACCT

TCCGTGTACC ACACTTCATA TATCATGAGT CACTTCATGT CTGGACATTA ACAAACTCTA TCTTAACATT

CAAATGCATG AGACTTTATC TCACTATAAA TGCACAATGA TTTAGCATTG TTTCTCACAA AACCATTCAA

GTTCATTAGT ACTACAACAA
```

>Gt13aΔ281 + CAAT                                                    SEQ ID NO: 3

```
TGAAACAATA TTATGAGTAA TGTGTGAGCA TTATGGGACC ACGAAATAAA AAAAGAACAT

TTTTATGAGC AGTGTGTTCT CAATGAGCCT TGAATGTTAT CACCCAGGAT AAGAAACCCT

TAAGCAATGA ACATGCAAG CGTTTAATGT GCAAAGTTGG CATTCTCCAC GACATAATGC

AAAAGAAGAT ATAATCTATG ACATAGCAAG TCATGCATCA TTTCATGCCT CTGTCAACCT

ATTCATTTCT AGTCATCTAG GTAAGTATCT TAAGCTAAAG TGTTAGAACT TCCCATACAT

AAGTCATAAC TGATGACAAT TGGGTGTAAC ACATGACCAA TACAAATGAT GTGTCAATTA

CACATGAGAG TCAAGCAAGA TAAAGCAAAA GGATGTGTAC ATAAAACTAC AGAGCTATAT

GTCATGTTGC GAAAAGAGGA GAGCTTATAA GACAAGCCAT GACTCAAAAA AAATTCACAT

GCCTACTGTG GCCCATATAT CATGCAACAA TCCAAAAACT CACAGGTCTC GGTGTTGATC

GTGTCAATAT GTGACCACCC TAAAAACTCT TCACTAAATA TTAAAGTATT GCTAGAACAG

AGCTTCAAGA TATAAGTCAT GATCACCAAC AATTATGTTC AAAAAGAAAT AGAAAGCTAT

GGCACAGCAA CAAAAAGCAA AAGCATGCAT GGATATAATC TTTAACATCA TCCATGTCAT

ATTGCAAAAG AAAGAAAGAG AGAACAATAC AAATGATGTG TCAATTACAC ATCCATCATT

ATCCATCCAC CTTCCGTGTA CCACACTTCA TATATCATGA GTCACTTCAT GTCTGGACAT

TAACAAACTC TATCTTAACA TTCAAATGCA TGAGACTTTA TCTCACTATA AATGCACAAT

GATTTAGCAT TGTTTCTCAC AAAACCATTC AAGTTCATTA GTACTACAAC AA
```

>Gt13aΔ281/Del                                                        SEQ ID NO: 4

```
TGAAACAATA TTATGAGTAA TGTGTGAGCA TTATGGGACC ACGAAATAAA AAAAGAACAT

TTTTATGAGC AGTGTGTTCT CAATGAGCCT TGAATGTTAT CACCCAGGAT AAGAAACCCT

TAAGCAATGA ACATGCAAG CGTTTAATGT GCAAAGTTGG CATTCTCCAC GACATAATGC

AAAAGAAGAT ATAATCTATG ACATAGCAAG TCATGCATCA TTTCATGCCT CTGTCAACCT

ATTCATTTCT AGTCATCTAG GTAAGTATCT TAAGCTAAAG TGTTAGAACT TCCCATACAT

GACAATTTGG TGTAACACAT GACAAACCAG AGAGTCAAGC AAGATAAAGC AAAAGGATGT

GTACATAAAA CTACAGAGCT ATATGTCATG TTGCGAAAAG AGGAGAGCTT ATAAGACAAG

CCATGACTCA AAAAAAATTC ACATGCCTAC TGTGGCCCAT ATATCATGCA ACAATCCAAA

AACTCACAGG TCTCGGTGTT GATCGTGTCA ACCACCCTA AAAACTCTTC ACTAAATATT

AAAGTATTGC TAGAACAGAG CTTCAAGATA TAAGTCATGA TCACCAACAA CCATGTTCAA

AAAGAAATAG AAAGCTATGG CACAGCAACA AAAAGCAAAA GCATGCATGG ATATAATCTT

TAACATCATC CATGTCATAT TGCAAAACAA TTAAAGAGAG AACAATACAA ATGATGTGTC

AATTACACAT CCATCATTAT CCATCCACCT TCCGTGTACC ACACTTCATA TATCATGAGT

CACTTCATGT CTGGACATTA ACAAACTCTA TCTTAACATT CAAATGCATG AGACTTTATC

TCACTATAAA TGCACAATGA TTTAGCATTG TTTCTCACAA AACCATTCAA GTTCATTAGT

ACTACAACAA
```

>Gt13aΔ281 + GCN4

-continued

SEQ ID NO: 5
TGAAACAATA TTATGAGTAA TGTGTGAGCA TTATGGGACC ACGAAATAAA AAAAGAACAT
TTTTATGAGC
AGTGTGTTCT CAATGAGCCT TGAATGTTAT CACCCAGGAT AAGAAACCCT TAAGCAATGA
AACATGCAAG
CGTTTAATGT GCAAAGTTGG CATTCTCCAC GACATAATGC AAAAGAAGAT ATAATCTATG
ACATAGCAAG
TCATGCATCA TTTCATGCCT CTGTCAACCT ATTCATTTCT AGTCATCTAG GTAAGTATCT
TAAGCTAAAG
TGTTAGAACT TCCCATACAT AAGTCATAAC TGATGACAAT TGGGTGTAAC ACATGACAAA
CCAGAGAGTC
AAGCAAGATA AAGCAAAAGG ATGTGTACAT AAAACTACAG AGCTATATGT CATGTTGCGA
AAAGAGGAGA
GCTTATAAGA CAAGCCATGA CTCAAAAAAA ATTCACATGC CTACTGTGGC CCATATATCA
TGCAACAATC
CAAAAACTCA CAGGTCTCGG TGTTGATCGT GTCAACATGT GACCACCCTA AAAACTCTTC
ACTAAATATT
AAAGTATTGC TAGAACAGAG CTTCAAGATA TAAGTCATGA TCACCAACAA CCATGTTCAA
AAAGAAATAG
AAAGCTATGG CACAGCAACA AAAAGCAAAA GCATGCATGG ATATAATCTT TAACATCATC
CATGTCATAT
TGCAAAAGAA AGAAAGAGAG AACAATACAA ATGATGTGTC AATTACACAT CCATCATTAT
CCATCCACCT
TCCGTGTACC ACACTTCATA TATCATGAGT CACTTCATAT ATCATGAGTC ACTTCATGTC
TGGACATTAA CAAACTCTAT CTTAACATTA ACAAACTCTA TCTTAACATT CAAATGCATG
AGACTTTATC TCACTATAAA TGCACAATGA TTTAGCATTG TTTCTCACAA AACCATTCAA
GTTCATTAGT ACTACAACAA

>Gt13a (Control)

SEQ ID NO: 6
TCACACCTTA TGTAAAGTAT TTGTTGCAAG AAAAGTCTAA GATGACAGCA ACCTGCTGAG AAGAACAACT
GACGATGTCA TAAGGAGAGG GAGCTTTTCG ATAGGTGCCG TGCAGTTCAA AGAGTTAGTT AGCAGTAGGA
TGAAGATTTT TGCACATGGC AATGAGAAGT TAATTATGGT GTAGGCAACC CAAATGAAAC ACCAAAATAT
GCACAAGACA GTTTGTTGTA TTCTGTAGTA CAGAATAAAC TAAAGTAATG AAAGAAGATG GTGTTAGAAA
ATGAAACAAT ATTATGAGTA ATGTGTGAGC ATTATGGGAC CACGAAATAA AAAAAGAACA TTTTTATGAG
CAGTGTGTTC TCAATGAGCC TTGAATGTTA TCACCCAGGA TAAGAAACCC TTAAGCAATG AAACATGCAA
GCGTTTAATG TGCAAAGTTG GCATTCTCCA CGACATAATG CAAAAGAAGA TATAATCTAT GACATAGCAA
GTCATGCATC ATTTCATGCC TCTGTCAACC TATTCATTTC TAGTCATCTA GGTAAGTATC TTAAGCTAAA
GTGTTAGAAC TTCCCATACA TAAGTCATAA CTGATGACAA TTGGGTGTAA CACATGACAA ACCAGAGAGT
CAAGCAAGAT AAAGCAAAAG GATGTGTACA TAAAACTACA GAGCTATATG TCATGTTGCG AAAAGAGGAG
AGCTTATAAG ACAAGCCATG ACTCAAAAAA ATTCACATG CCTACTGTGG CCCATATATC ATGCAACAAT
CCAAAAACTC ACAGGTCTCG GTGTTGATCG TGTCAACATG TGACCACCCT AAAAACTCTT CACTAAATAT
TAAAGTATTG CTAGAACAGA GCTTCAAGAT ATAAGTCATG ATCACCAACA ACCATGTTCA AAAAGAAATA

```
GAAAGCTATG GCACAGCAAC AAAAAGCAAA AGCATGCATG GATATAATCT TTAACATCAT CCATGTCATA

TTGCAAAAGA AGAAAGAGA GAACAATACA AATGATGTGT CAATTACACA TCCATCATTA TCCATCCACC

TTCCGTGTAC CACACTTCAT ATATCATGAG TCACTTCATG TCTGGACATT AACAAACTCT ATCTTAACAT

TCAAATGCAT GAGACTTTAT CTCACTATAA ATGCACAATG ATTTAGCATT GTTTCTCACA AAACCATTCA

AGTTCATTAG TACTACAACA A
```

\>FSA-DNA

SEQ ID NO: 7

```
GAGTCTAGCG GAGGCCCACC AGAGCGAGAT CGCCCACCGC TTCAACGACC TCGGCGAGGA GCACTTCCGC

GGCCTCGTGC TCGTGGCCTT CAGCCAGTAC CTCCAGCAGT GCCCGTTCGA GGACCACGTG AAGCTCGTGA

ACGAGGTGAC CGAGTTCGCC AAGGGCTGCG TGGCCGACCA GAGCGCCGCC AACTGCGAGA GAGCCTCCA

CGAGCTCCTC GGCGACAAGC TCTGCACCGT GGCCAGCCTC CGCGACAAGT ACGGCGAGAT GGCCGACTGC

TGCGAGAAGA AGGAGCCGGA GCGCAACGAG TGCTTCCTCC AGCACAAGGA CGACAACCCG GGCTTCGGCC

AGCTCGTGAC CCCGGAGGCC GACGCCATGT GCACCGCCTT CCACGAGAAC GAGCAGCGCT TCCTCGGCAA

GTACCTCTAC GAGATCGCCC GCCGCCACCC GTACTTCTAC GCCCCGGAGC TCCTCTACTA CGCCGAGGAG

TACAAGGGCG TGTTCACCGA GTGCTGCGAG GCCGCCGACA AGGCCGCCTG CCTCACCCCG AAGGTGGACG

CCCTCCGCGA GAAGGTGCTC GCCAGCAGCG CCAAGGAGCG CCTCAAGTGC GCCAGCCTCC AGAAGTTCGG

CGAGCGCGCC TTCAAGGCCT GGAGCGTGGC CCGCCTCAGC CAGAAGTTCC GAAGGCCGA GTTCGCCGAG

ATCAGCAAGC TCGTGACCGA CCTCGCCAAG ATCCACAAGG AGTGCTGCCA CGGCGACCTC CTAGAGTGCG

CCGACGACCG CGCCGACCTC GCCAAGTACA TCTGCGAGAA CCAGGACAGC ATCAGCACCA AGCTCAAGGA

GTGCTGCGGC AAGCCGGTGC TAGAGAAGAG CCACTGCATC AGCGAGGTGG AGCGCGACGA GCTCCCGGCC

GACCTCCCGC CGCTCGCCGT GGACTTCGTG GAGGACAAGG AGGTGTGCAA GAACTACCAG GAGGCCAAGG

ACGTGTTCCT CGGCACCTTC CTCTACGAGT ACAGCCGCCG CCACCCGGAG TACAGCGTGA GCCTCCTCCT

CCGCCTCGCC AAGGAGTACG AGGCCACCCT AGAGAAGTGC TGCGCCACCG ACGACCCGCC GGCCTGCTAC

GCCCACGTGT TCGACGAGTT CAAGCCGCTC GTGGAGGAGC CGCACAACCT CGTGAAGACC AACTGCGAGC

TCTTCGAGAA GCTCGGCGAG TACGGCTTCC AGAACGCCCT CCTCGTGCGC TACACCAAGA AGGTGCCGCA

GGTGAGCACC CCGACCCTCG TGGAGGTGAG CCGCAGCCTC GGCAAGGTGG GCAGCAAGTG CTGCACCCAC

CCGGAGGCCG AGCGCCTCAG CTGCGCCGAG GACTACCTCA GCGTGGTGCT CAACCGCCTC TGCGTGCTCC

ACGAGAAGAC CCCGGTGAGC GAGCGCGTGA CCAAGTGCTG CACCGAGAGC CTCGTGAACC GCCGCCCGTG

CTTCAGCGCC CTCCAGGTGG ACGAGACCTA CGTGCCGAAG GAGTTCAGCG CCGAGACCTT CACCTTCCAC

GCCGACCTCT GCACCCTCCC GGAGGCCGAG AAGCAGATCA AGAAGCAGAG CGCCCTCGTG GAGCTCCTCA

AGCACAAGCC GAAGGCCACC GAGGAGCAGC TCAAGACCGT GATGGGCGAC TTCGGCAGCT TCGTGGACAA

GTGCTGCGCC GCCGAGGACA AGGAGGCCTG CTTCGCCGAG GAGGGCCCGA AGCTCGTGGC CGCCGCCCAG

GCCGCCCTCG CCTGAGCTCG AG
```

\>FSA-AA

SEQ ID NO: 8

```
EAHQSEIAHR FNDLGEEHFR GLVLVAFSQY LQQCPFEDHV KLVNEVTEFA KGCVADQSAA NCEKSLHELL

GDKLCTVASL RDKYGEMADC CEKKEPERNE CFLQHKDDNP GFGQLVTPEA DAMCTAFHEN EQRFLGKYLY

EIARRHPYFY APELLYYAEE YKGVFTECCE AADKAACLTP KVDALREKVL ASSAKERLKC ASLQKFGERA

FKAWSVARLS QKFPKAEFAE ISKLVTDLAK IHKECCHGDL LECADDRADL AKYICENQDS ISTKLKECCG

KPVLEKSHCI SEVERDELPA DLPPLAVDFV EDKEVCKNYQ EAKDVFLGTF LYEYSRRHPE YSVSLLLRLA

KEYEATLEKC CATDDPPACY AHVFDEFKPL VEEPHNLVKT NCELFEKLGE YGFQNALLVR YTKKVPQVST

PTLVEVSRSL GKVGSKCCTH PEAERLSCAE DYLSVVLNRL CVLHEKTPVS ERVTKCCTES LVNRRPCFSA

LQVDETYVPK EFSAETFTFH ADLCTLPEAE KQIKKQSALV ELLKHKPKAT EEQLKTVMGD FGSFVDKCCA
```

AEDKEACFAE EGPKLVAAAQ AALA

>Forward primer

SEQ ID NO: 9

AGCTACCAGG GCAACAGCGA

>Reverse primer

SEQ ID NO: 10

ATCTCGTAGA GGTACTTGCC GA

---

What is claimed is:

1. A non-natural plant endosperm-specific expression promoter, having the nucleotide sequence as set forth in SEQ ID NO:2, SEQ ID NO:3, SEQ ID NO:4 or SEQ ID NQ:5.

2. An expression cassette comprising or having contained therein the plant endosperm-specific expression promoter of claim 1.

3. A recombinant expression vector comprising the non-natural plant endosperm-specific expression promoter of claim 1.

4. A host *agrobacterium* comprising the non-natural plant endosperm-specific expression promoter of claim 1.

5. A transgenic plant, plant cell or cell line, comprising the non-natural plant endosperm-specific expression promoter of claim 1.

6. A method for preparing a genetically engineered plant or transgenic plant comprising inserting into a cell of the plant the heterologous or exogenous nucleic acid comprising a nonnatural plant endosperm-specific expression promoter of claim 1.

7. The method of claim 6, wherein the promoter is operably linked to a nucleic acid capable of expressing a recombinant protein or metabolite.

8. The method of claim 6, wherein the plant is a rice, wheat, corn, barley, chestnut, sorghum or oats monocotyledonous plant.

9. The method of claim 6, wherein the plant is a soybean, rape or sunflower dicotyledonous plant.

10. A method of preparing a recombinant protein using the plant endosperm-specific expression promoter of claim 1, the method comprising:
   1) constructing a rice endosperm cell-specific intermediate vector comprising incorporation into the vector the non-natural plant endosperm-specific expression promoter of claim 1;
   2) synthesizing a nucleic acid encoding the recombinant protein;
   3) operably ligating the vector of step 1) with the nucleic acid of step 2), to obtain a vector for recombinant protein expression mediated by the promoter of claim 1;
   4) transforming a plant comprising an endosperm with the expression vector of step 3) and expressing the recombinant protein in the plant endosperm;
   5) extracting and/or purifying the recombinant protein from the plant.

11. The method of claim 10, wherein the recombinant protein is a feline serum albumin.

12. The non-natural plant endosperm-specific expression promoter of claim 1, wherein the promoter comprises the nucleotide sequence as set forth in SEQ ID NO:2.

13. The non-natural plant endosperm-specific expression promoter of claim 1, wherein the promoter comprises the nucleotide sequence as set forth in SEQ ID NO:3.

14. The non-natural plant endosperm-specific expression promoter of claim 1, wherein the promoter comprises the nucleotide sequence as set forth in SEQ ID NO:4.

15. The non-natural plant endosperm-specific expression promoter of claim 1, wherein the promoter comprises the nucleotide sequence as set forth in SEQ ID NO:5.

16. The non-natural plant endosperm-specific expression promoter of claim 1, wherein the promoter consists essentially of the nucleotide sequence as set forth in SEQ ID NO:2, SEQ ID NO:3, SEQ ID NO:4 or SEQ ID NO:5.

17. The non-natural plant endosperm-specific expression promoter of claim 1, wherein the promoter is operably linked to a heterologous or exogenous nucleic acid.

18. The non-natural plant endosperm-specific expression promoter of claim 17, wherein the heterologous or exogenous nucleic acid encodes or synthesizes a heterologous protein or a metabolite.

19. A recombinant plant having contained therein a heterologous or exogenous nucleic acid comprising a non-natural plant endosperm-specific expression promoter of claim 1.

20. The plant of claim 19, wherein if the plant is a monocotyledonous plant, the plant is rice, wheat, corn, barley, chestnut, sorghum or oats.

* * * * *

SEQUENCE LISTING

```
Sequence total quantity: 10
SEQ ID NO: 1          moltype = DNA   length = 930
FEATURE               Location/Qualifiers
source                1..930
                      mol_type = other DNA
                      organism = synthetic construct
SEQUENCE: 1
tgaaacaata ttatgagtaa tgtgtgagca ttatgggacc acgaaataaa aaaagaacat  60
ttttatgagc agtgtgttct caatgagcct tgaatgttat cacccaggat aagaaaccct 120
taagcaatga aacatgcaag cgtttaatgt gcaaagttgg cattctccac gacataatgc 180
aaaagaagat ataatctatg acatagcaag tcatgcatca tttcatgcct ctgtcaacct 240
attcatttct agtcatctag gtaagtatct taagctaaag tgttagaact tcccatacat 300
aagtcataac tgatgacaat tgggtgtaac acatgacaaa ccagagagtc aagcaagata 360
aagcaaaagg atgtgtacat aaaactacag agctatatgt catgttgcga aaagaggaga 420
gcttataaga caagccatga ctcaaaaaaa attcacatgc ctactgtggc ccatatatca 480
tgcaacaatc caaaaactca caggtctcgg tgttgatcgt gtcaacatgt gaccaccta  540
aaaactcttc actaaatatt aaagtattgc tagaacagag cttcaagata taagtcatga 600
tcaccaacaa ccatgttcaa aaagaaatag aaagctatgg cacagcaaca aaaagcaaaa 660
gcatgcatgg atataatctt taacatcatc catgtcatat tgcaaaagaa agaaagagag 720
aacaatacaa atgatgtgtc aattacacat ccatcattat ccatccacct tccgtgtacc 780
acacttcata tatcatgagt cacttcatgt ctggacatta acaaactcta tcttaacatt 840
caaatgcatg agactttatc tcactataaa tgcacaatga tttagcattg tttctcacaa 900
aaccattcaa gttcattagt actacaacaa                                  930

SEQ ID NO: 2          moltype = DNA   length = 930
FEATURE               Location/Qualifiers
source                1..930
                      mol_type = other DNA
                      organism = synthetic construct
SEQUENCE: 2
tgaaacaata ttatgagtaa tgtgtgagca ttatgggacc acgaaataaa aaaagaacat  60
ttttatgagc agtgtgttct caatgagcct tgaatgttat cacccaggat aagaaaccct 120
taagcaatga aacatgcaag cgtttaatgt gcaaagttgg cattctccac gacataatgc 180
aaaagaagat ataatctatg acatagcaag tcatgcatca tttcatgcct ctgtcaacct 240
attcatttct agtcatctag gtaagtatct taagctaaag tgttagaact tcccatacat 300
aagtcataac tgatgacaat ttggtgtaac acatgacaaa ccagagagtc aagcaagata 360
aagcaaaagg atgtgtacat aaaactacag agctatatgt catgttgcga aaagaggaga 420
gcttataaga caagccatga ctcaaaaaaa attcacatgc ctactgtggc ccatatatca 480
tgcaacaatc caaaaactca caggtctcgg tgttgatcgt gtcaacatgt gaccaccta  540
aaaactcttc actaaatatt aaagtattgc tagaacagag cttcaagata taagtcatga 600
tcaccaacaa ccatgttcaa aaagaaatag aaagctatgg cacagcaaca aaaagcaaaa 660
gcatgcatgg atataatctt taacatcatc catgtcatat tgcaaaataa ataagagag  720
aacaatacaa atgatgtgtc aattacacat ccatcattat ccatccacct tccgtgtacc 780
acacttcata tatcatgagt cacttcatgt ctggacatta acaaactcta tcttaacatt 840
caaatgcatg agactttatc tcactataaa tgcacaatga tttagcattg tttctcacaa 900
aaccattcaa gttcattagt actacaacaa                                  930

SEQ ID NO: 3          moltype = DNA   length = 952
FEATURE               Location/Qualifiers
source                1..952
                      mol_type = other DNA
                      organism = synthetic construct
SEQUENCE: 3
tgaaacaata ttatgagtaa tgtgtgagca ttatgggacc acgaaataaa aaaagaacat  60
ttttatgagc agtgtgttct caatgagcct tgaatgttat cacccaggat aagaaaccct 120
taagcaatga aacatgcaag cgtttaatgt gcaaagttgg cattctccac gacataatgc 180
aaaagaagat ataatctatg acatagcaag tcatgcatca tttcatgcct ctgtcaacct 240
attcatttct agtcatctag gtaagtatct taagctaaag tgttagaact tcccatacat 300
aagtcataac tgatgacaat tgggtgtaac acatgaccaa tacaaatgat gtgtcaatta 360
cacatgagag tcaagcaaga taaagcaaaa ggatgtgtac ataaaactac agctatatat 420
gtcatgttgc gaaaagagga gagcttataa gacaagccat gactcaaaaa aaattcacat 480
gcctactgtg gcccatatat catgcaacaa tccaaaaact cacaggtctc ggtgttgatc 540
gtgtcaatat gtgaccaccc taaaaactct tcactaaata ttaaagtatt gctagaacag 600
agcttcaaga tataagtcat gatcaccaac aattatgttc aaaaagaaat agaaagctat 660
```

```
ggcacagcaa caaaaagcaa aagcatgcat ggatataatc tttaacatca tccatgtcat   720
attgcaaaag aaagaaagag agaacaatac aaatgatgtg tcaattacac atccatcatt   780
atccatccac cttccgtgta ccacacttca tatatcatga gtcacttcat gtctggacat   840
taacaaactc tatcttaaca ttcaaatgca tgagacttta tctcactata aatgcacaat   900
gatttagcat tgtttctcac aaaaccattc aagttcatta gtactacaac aa            952

SEQ ID NO: 4            moltype = DNA   length = 910
FEATURE                 Location/Qualifiers
source                  1..910
                        mol_type = other DNA
                        organism = synthetic construct
SEQUENCE: 4
tgaaacaata ttatgagtaa tgtgtgagca ttatgggacc acgaaataaa aaaagaacat    60
ttttatgagc agtgtgttct caatgagcct tgaatgttat cacccaggat aagaaaccct   120
taagcaatga acatgcaag cgtttaatgt gcaaagttgg cattctccac gacataatgc   180
aaaagaagat ataatctatg acatagcaag tcatgcatca tttcatgcct ctgtcaacct   240
attcatttct agtcatctag gtaagtatct taagctaaag tgttagaact tcccatacat   300
gacaatttgg tgtaacacat gacaaaccag agagtcaagc aagataaagc aaaaggatgt   360
gtacataaaa ctacagagct atatgtcatg ttgcgaaaag aggagagctt ataagacaag   420
ccatgactca aaaaaaattc acatgcctac tgtggcccat atatcatgca acaatccaaa   480
aactcacagg tctcggtgtt gatcgtgtca accacccta aaaactcttc actaaatatt    540
aaagtattgc tagaacagag cttcaagata taagtcatga tcaccaacaa ccatgttcaa   600
aaagaaatag aaagctatgg cacagcaaca aaaagcaaaa gcatgcatgg atataatctt   660
taacatcatc catgtcatat tgcaaaacaa ttaaagagag aacaatacaa atgatgtgtc   720
aattacacat ccatcattat ccatccacct tccgtgtacc acacttcata tatcatgagt   780
cacttcatgt ctggacatta acaaactcta tcttaacatt caaatgcatg agactttatc   840
tcactataaa tgcacaatga tttagcattg tttctcacaa aaccattcaa gttcattagt   900
actacaacaa                                                          910

SEQ ID NO: 5            moltype = DNA   length = 970
FEATURE                 Location/Qualifiers
source                  1..970
                        mol_type = other DNA
                        organism = synthetic construct
SEQUENCE: 5
tgaaacaata ttatgagtaa tgtgtgagca ttatgggacc acgaaataaa aaaagaacat    60
ttttatgagc agtgtgttct caatgagcct tgaatgttat cacccaggat aagaaaccct   120
taagcaatga acatgcaag cgtttaatgt gcaaagttgg cattctccac gacataatgc   180
aaaagaagat ataatctatg acatagcaag tcatgcatca tttcatgcct ctgtcaacct   240
attcatttct agtcatctag gtaagtatct taagctaaag tgttagaact tcccatacat   300
aagtcataac tgatgacaat tgggtgtaac acatgacaaa ccagagagtc aagcaagata   360
aagcaaaagg atgtgtacat aaaactcag agctatatgt catgttgcga aaagaggaga   420
gcttataaga caagccatga ctcaaaaaaa attcacatgc ctactgtggc ccatatatca   480
tgcaacaatc caaaaactca caggtctcgg tgttgatcgt gtcaacatgt gaccacccta   540
aaaactcttc actaaatatt aaagtattgc tagaacagag cttcaagata taagtcatga   600
tcaccaacaa ccatgttcaa aaagaaatag aaagctatgg cacagcaaca aaaagcaaaa   660
gcatgcatgg atataatctt taacatcatc catgtcatat tgcaaaagaa agaaagagag   720
aacaatacaa atgatgtgtc aattacacat ccatcattat ccatccacct tccgtgtacc   780
acacttcata tatcatgagt cacttcatat atcatgagtc acttcatgtc tggacattaa   840
caaactctat cttaacatta caaactcta tcttaacatt caaatgcatg agactttatc   900
tcactataaa tgcacaatga tttagcattg tttctcacaa aaccattcaa gttcattagt   960
actacaacaa                                                          970

SEQ ID NO: 6            moltype = DNA   length = 1211
FEATURE                 Location/Qualifiers
source                  1..1211
                        mol_type = other DNA
                        organism = Oryza sativa
SEQUENCE: 6
tcacacctta tgtaaagtat ttgttgcaag aaaagtctaa gatgacagca acctgctgag    60
aagaacaact gacgatgtca taggagagg gagcttttcg ataggtgccg tgcagttcaa   120
agagttagtt agcagtagga tgaagatttt tgcacatggc aatgagaagt taattatggt   180
gtaggcaacc caaatgaaac accaaaatat gcacaagaca gtttgttgta ttctgtagta   240
cagaataaac taaagtaaaa aaagaagatg tgttagaaac attgaacaat attatgagta   300
atgtgtgagc attatgggac cacgaaataa aaaagaaca ttttatgag cagtgtgttc   360
tcaatgagcc ttgaatgtta tcacccagga taagaaaccc ttaagcaatg aaacatgcaa   420
gcgtttaatg tgcaaagttg gcattctcca cgacataatg caaaagaaga tataatctat   480
gacatagcaa gtcatgcatc atttcatgcc tctgtcaacc tattcatttc tagtcatctag   540
ggtaagtatc ttaagctaaa gtgttagaac ttcccataca taagtcataa ctgatgacaa   600
ttgggtgtaa cacatgacaa accagagagt caagcaagat aaagcaaaag gatgtgtaca   660
taaaactaca gagctatatg tcatgttgcg aaaagaggag agcttataag acaagccatg   720
actcaaaaaa aattcacatg cctactgtgg cccatatatc atgcaacaat ccaaaaactc   780
acaggtctcg gtgttgatcg tgtcaacatg tgaccaccct aaaaactctt cactaaatat   840
taaagtattg ctagaacaga gcttcaagat ataagtcacc aaccatgttca           900
aaaagaaata gaaagctatg gcacagcaac aaaaagcaaa agcatgcatg gatataatct   960
ttaacatcat ccatgtcata ttgcaaaaga agaaagaga gaacaataca aatgatgtgt   1020
caattacaca tccatcatta tccatccacc ttccgtgtac cacacttcat atatcatgag   1080
tcacttcatg tctggacatt aacaaactct atcttaacat tcaaatgcat gagactttat   1140
ctcactataa atgcacaatg atttagcatt gtttctcaca aaaccattca agttcattag   1200
```

```
tactacaaca a                                                                1211

SEQ ID NO: 7            moltype = DNA  length = 1772
FEATURE                 Location/Qualifiers
source                  1..1772
                        mol_type = other DNA
                        organism = synthetic construct
SEQUENCE: 7
gagtctagcg gaggcccacc agagcgagat cgcccaccgc ttcaacgacc tcggcgagga        60
gcacttccgc ggcctcgtgc tcgtggcctt cagccagtac ctccagcagt gcccgttcga       120
ggaccacgtg aagctcgtga acgaggtgac cgagttcgcc aagggctgcg tggccgacca       180
gagcgccgcc aactgcgaga agagcctcca cgagctcctc ggcgacaagc tctgcaccgt       240
ggccagcctc cgcgacaagt acggcgagat ggccgactgc tgcgagaaga aggagccgga       300
gcgcaacgag tgcttcctcc agcacaagga cgacaacccg ggcttcggcc agctcgtgac       360
cccggaggcc gacgccatgt gcaccgcctt ccacgagaac gagcagcgct tcctcggcaa       420
gtacctctac gagatcgccc gccgccaccc gtacttctac gccccggagc tcctctacta       480
cgccgaggag tacaagggcg tgttcaccga gtgctgcgag gccgccgaca aggccgcctg       540
cctcaccccg aaggtggacg ccctccgcga gaaggtgctc gccagcagcg ccaaggagcg       600
cctcaagtgc gccagcctcc agaagttcgg cgagcgcgcc ttcaaggcct ggagcgtggc       660
ccgcctcagc cagaagttcc cgaaggccga gttcgccgag atcagcaagc tcgtgaccga       720
cctcgccaag atccacaagg agtgctgcca cggcgacctc ctagagtgcg ccgacgaccg       780
cgccgacctc gccaagtaca tctgcgagaa ccaggacagc atcagcacca agctcaagga       840
gtgctgcggc aagccggtgc tagagaagag ccactgcatc agcgaggtgg agcgcgacga       900
gctcccggcc gacctcccgc cgctcgccgt ggacttcgtg gaggacaagg aggtgtgcaa       960
gaactaccag gaggccaagg acgtgttcct cggcaccttc ctctacgagt acagccgccg      1020
ccacccggag tacgacgtga gcctcctcct ccgcctcgcc aaggagtacg aggccaccct      1080
agagaagtgc tgcgccaccg acgacccgcc ggcctgctac gcccacgtgt tcgacgagtt      1140
caagccgctc gtggaggagc cgcacaacct cgtgaagacc aactgcgagc tcttcgagaa      1200
gctcggcgag tacggcttcc agaacgccct cctcgtgcgc tacaccaaga aggtgccgca      1260
ggtgagcacc ccgaccctcg tggaggtgag ccgcagcctc ggcaaggtgg gcaagaagtg      1320
ctgcacccac ccggaggccg agcgcctcag ctgcgccgag gactacctca gcgtggtgct      1380
caaccgcctc tgcgtgctcc acgagaagac cccggtgagc gagcgcgtga ccaagtgctg      1440
caccgagagc ctcgtgaacc gccgccgtg cttcagcgcc ctccaggtgg acgagaccta      1500
cgtgccgaag gagttcagcg ccgagacctt caccttccac gccgacctct gcaccctccc      1560
ggaggccgag aagcagatca agaagcagag cgccctcgtg gagctcctca agcacaagcc      1620
gaaggccacc gaggagcagc tcaagaccgt gatgggcgac ttcggcagct tcgtggacaa      1680
gtgctgcgcc gccgaggaca aggaggcctg cttcgccgag gagggcccga agctcgtggc      1740
cgccgcccag gccgccctcg cctgagctcg ag                                   1772

SEQ ID NO: 8            moltype = AA  length = 584
FEATURE                 Location/Qualifiers
source                  1..584
                        mol_type = protein
                        organism = Felis catus
SEQUENCE: 8
EAHQSEIAHR FNDLGEEHFR GLVLVAFSQY LQQCPFEDHV KLVNEVTEFA KGCVADQSAA        60
NCEKSLHELL GDKLCTVASL RDKYGEMADC CEKKEPERNE CFLQHKDDNP GFGQLVTPEA       120
DAMCTAFHEN EQRFLGKYLY EIARRHPYFY APELLYYAEE YKGVFTECCE AADKAACLTP       180
KVDALREKVL ASSAKERLKC ASLQKFGERA FKAWSVARLS QKFPKAEFAE ISKLVTDLAK       240
IHKECCHGDL LECADDRADL AKYICENQDS ISTKLKECCG KPVLEKSHCI SEVERDELPA       300
DLPPLAVDFV EDKEVCKNYQ EAKDVFLGTF LYEYSRRHPE YSVSLLLRLA KEYEATLEKC       360
CATDDPPACY AHVFDEFKPL VEEPHNLVKT NCELFEKLGE YGFQNALLVR YTKKVPQVST       420
PTLVEVSRSL GKVGSKCCTH PEAERLSCAE DYLSVVLNRL CVLHEKTPVS ERVTKCCTES       480
LVNRRPCFSA LQVDETYVPK EFSAETFTFH ADLCTLPEAE KQIKKQSALV ELLKHKPKAT       540
EEQLKTVMGD FGSFVDKCCA AEDKEACFAE EGPKLVAAAQ AALA                       584

SEQ ID NO: 9            moltype = DNA  length = 20
FEATURE                 Location/Qualifiers
source                  1..20
                        mol_type = other DNA
                        organism = synthetic construct
SEQUENCE: 9
agctaccagg gcaacagcga                                                    20

SEQ ID NO: 10           moltype = DNA  length = 22
FEATURE                 Location/Qualifiers
source                  1..22
                        mol_type = other DNA
                        organism = synthetic construct
SEQUENCE: 10
atctcgtaga ggtacttgcc ga                                                 22
```